United States Patent
Matsui et al.

(10) Patent No.: US 10,321,901 B2
(45) Date of Patent: Jun. 18, 2019

(54) MEDICAL INSTRUMENT THAT WIRELESSLY RECEIVES POWER, INSERTION ASSISTING TOOL THAT WIRELESSLY TRANSMITS POWER AND MEDICAL SYSTEM

(71) Applicant: OLYMPUS CORPORATION, Tokyo (JP)

(72) Inventors: Akira Matsui, Hino (JP); Yuta Sugiyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 343 days.

(21) Appl. No.: 15/299,632

(22) Filed: Oct. 21, 2016

(65) Prior Publication Data
US 2017/0035402 A1 Feb. 9, 2017

Related U.S. Application Data

(63) Continuation of application No. PCT/JP2015/052993, filed on Feb. 3, 2015.

(30) Foreign Application Priority Data

Apr. 21, 2014 (JP) .................................. 2014-087564

(51) Int. Cl.
*A61B 18/12* (2006.01)
*A61B 1/00* (2006.01)
(Continued)

(52) U.S. Cl.
CPC .... *A61B 17/00234* (2013.01); *A61B 1/00029* (2013.01); *A61B 1/00114* (2013.01);
(Continued)

(58) Field of Classification Search
CPC ..... A61B 1/018; A61B 1/005; A61B 1/00071; A61B 1/00029; A61B 1/00027;
(Continued)

(56) References Cited

U.S. PATENT DOCUMENTS 4,240,010 A * 12/1980 Buhrer .................. H01J 65/048
313/493
5,021,914 A * 6/1991 Tsurunaga .............. H01L 39/16
335/216
(Continued)

FOREIGN PATENT DOCUMENTS

EP 2 031 731 A1 3/2009
JP H11-128242 A 5/1999
(Continued)

OTHER PUBLICATIONS

International Search Report dated Apr. 28, 2015 issued in International Application No. PCT/JP2015/052993.

*Primary Examiner* — John P Leubecker
(74) *Attorney, Agent, or Firm* — Scully, Scott, Murphy & Presser, P.C.

(57) ABSTRACT

A treatment instrument includes a power receiver and a treatment section configured to be driven by power received by the power receiver. The power receiver includes a first solenoid-shaped power receiving coil and a second solenoid-shaped power receiving coil having a winding direction opposite to a winding direction of the first power receiving coil. The first power receiving coil and the second power receiving coil have the same length and the same number of turns, and are arranged concentrically. The first power receiving coil and the second power receiving coil are electrically connected to a treatment section so that a direction in which a current flows through the first power receiv-
(Continued)

ing coil is opposite to a direction in which a current flows through the second power receiving coil.

9 Claims, 5 Drawing Sheets

(51) Int. Cl.

| | | |
|---|---|---|
| *A61B 17/34* | (2006.01) | |
| *A61B 17/00* | (2006.01) | |
| *H02J 50/70* | (2016.01) | |
| *H02J 50/12* | (2016.01) | |
| *H02J 50/10* | (2016.01) | |
| *A61B 10/06* | (2006.01) | |
| *A61B 17/16* | (2006.01) | |
| *A61B 17/22* | (2006.01) | |
| *A61B 17/28* | (2006.01) | |
| *A61B 17/32* | (2006.01) | |
| *A61B 18/14* | (2006.01) | |
| *A61N 7/00* | (2006.01) | |

(52) U.S. Cl.
CPC ............. *A61B 10/06* (2013.01); *A61B 17/16* (2013.01); *A61B 17/2202* (2013.01); *A61B 17/28* (2013.01); *A61B 17/320068* (2013.01); *A61B 17/34* (2013.01); *A61B 17/3421* (2013.01); *A61B 18/14* (2013.01); *A61N 7/00* (2013.01); *H02J 50/10* (2016.02); *H02J 50/12* (2016.02); *H02J 50/70* (2016.02); *A61B 17/3476* (2013.01); *A61B 18/1206* (2013.01); *A61B 18/1442* (2013.01); *A61B 2018/1286* (2013.01)

(58) Field of Classification Search
CPC .... A61B 2560/0204; A61B 2560/0217; A61B 2018/00077; A61B 2018/00178; A61B 2018/00982; A61B 2017/0034; A61B 17/3476; H02J 50/05; H02J 50/12; H02J 50/70
See application file for complete search history.

(56) References Cited

U.S. PATENT DOCUMENTS

| | | | | |
|---|---|---|---|---|
| 5,157,576 | A * | 10/1992 | Takaya | H01F 17/0006 257/531 |
| 6,187,002 | B1 * | 2/2001 | Long | A61B 18/1487 606/46 |
| 6,206,875 | B1 * | 3/2001 | Long | A61B 18/1487 606/41 |
| 2005/0154294 | A1 * | 7/2005 | Uchiyama | A61B 1/00029 600/420 |
| 2007/0216377 | A1 * | 9/2007 | Yoshimura | H04L 25/0266 323/250 |
| 2009/0085408 | A1 | 4/2009 | Bruhn | |
| 2011/0025132 | A1 * | 2/2011 | Sato | H02J 5/005 307/104 |
| 2011/0094994 | A1 * | 4/2011 | Todorow | H01J 37/321 216/68 |
| 2011/0115891 | A1 * | 5/2011 | Trusty | A61B 1/00016 348/65 |
| 2015/0022147 | A1 * | 1/2015 | Jung | H02J 5/005 320/108 |
| 2015/0145341 | A1 * | 5/2015 | Chiyo | H01F 27/38 307/104 |
| 2015/0366610 | A1 * | 12/2015 | Tsuruta | A61B 1/00029 606/46 |
| 2018/0252551 | A1 * | 9/2018 | Xie | G01D 3/028 |

FOREIGN PATENT DOCUMENTS

| | | |
|---|---|---|
| JP | 2009-111977 A | 5/2009 |
| JP | 2011-259534 A | 12/2011 |
| JP | 2014-004237 A | 1/2014 |
| JP | 2014-150628 A | 8/2014 |
| WO | WO 2014/002830 A1 | 1/2014 |
| WO | 2014/118615 A2 | 8/2014 |

* cited by examiner

MEDICAL INSTRUMENT THAT WIRELESSLY RECEIVES POWER, INSERTION ASSISTING TOOL THAT WIRELESSLY TRANSMITS POWER AND MEDICAL SYSTEM

CROSS REFERENCE TO RELATED APPLICATION

This application is a continuation application of PCT/JP2015/052993 filed on Feb. 3, 2015 and claims benefit of Japanese Application No. 2014-087564 filed in Japan on Apr. 21, 2014, the entire contents of which are incorporated herein by this reference.

BACKGROUND OF THE INVENTION

1. Field of the Invention

The present invention relates to a medical instrument that wirelessly receives power, an insertion assisting tool that transmits power to the medical instrument and a medical system equipped with the medical instrument and the insertion assisting tool.

2. Description of the Related Art

A trocar, which is an insertion assisting tool, is integrally combined with an inner needle having a sharp puncture needle at a distal end thereof is inserted into an abdominal cavity with the inner needle being punctured into a patient's body wall. After being inserted into the abdominal cavity, the inner needle is pulled out and the trocar is thereby placed on the body wall and used as a guide tube for a medical instrument for performing treatment inside the abdominal cavity.

A cable for supplying power necessary for the treatment may be connected to the medical instrument inserted into the body of the subject via an insertion hole of the trocar. Such a cable, however, causes operability to deteriorate when an operator conducts an operation.

As a method for solving this problem, Japanese Patent Application Laid-Open Publication No. 11-128242 discloses that power is wirelessly supplied to a power receiving coil of a medical instrument inserted into a trocar and electromagnetically coupled with a power transmitting coil via an alternating magnetic field generated from the power transmitting coil of the trocar.

SUMMARY OF THE INVENTION

A medical instrument according to an embodiment is provided with a power receiver including a power receiving circuit configured to magnetically couple with an alternating magnetic field and receive power and a drive circuit configured to be driven by the power received by the power receiver, in which the power receiver includes a first solenoid-shaped power receiving coil and a second solenoid-shaped power receiving coil having a winding direction opposite to a winding direction of the first power receiving coil, the first power receiving coil and the second power receiving coil have the same length and the same number of turns, and are arranged concentrically, and the first power receiving coil and the second power receiving coil are electrically connected to the power receiving circuit so that a direction in which a current flows through the first power receiving coil is opposite to a direction in which a current flows through the second power receiving coil.

An insertion assisting tool according to another embodiment is provided with a power transmitter configured to generate an alternating magnetic field to be applied to a medical instrument inserted into an insertion hole, in which the power transmitter includes a first solenoid-shaped power transmitting coil and a second solenoid-shaped power transmitting coil having a winding direction opposite to a winding direction of the first power transmitting coil, the first power transmitting coil and the second power transmitting coil have the same length and the same number of turns, and are arranged concentrically, and the first power transmitting coil and the second power transmitting coil are electrically connected to a power supply device so that a direction in which a current flows through the first power transmitting coil is opposite to a direction in which a current flows through the second power transmitting coil.

A medical system according to a further embodiment is provided with an insertion assisting tool including a power transmitter configured to generate an alternating magnetic field, a power receiver including a power receiving circuit configured to magnetically couple with the alternating magnetic field when inserted into an insertion hole of the insertion assisting tool and receive power, and the medical instrument including a drive circuit configured to be driven by the power received by the power receiver, in which the power receiver includes a first solenoid-shaped power receiving coil and a second solenoid-shaped power receiving coil having a winding direction opposite to a winding direction of the first power receiving coil, the first power receiving coil and the second power receiving coil have the same length and the same number of turns, and are arranged concentrically, and the first power receiving coil and the second power receiving coil are electrically connected to the power receiving circuit so that a direction in which a current flows through the first power receiving coil is opposite to a direction in which a current flows through the second power receiving coil.

DETAILED DESCRIPTION OF THE PREFERRED EMBODIMENT

First Embodiment

Figure 1:
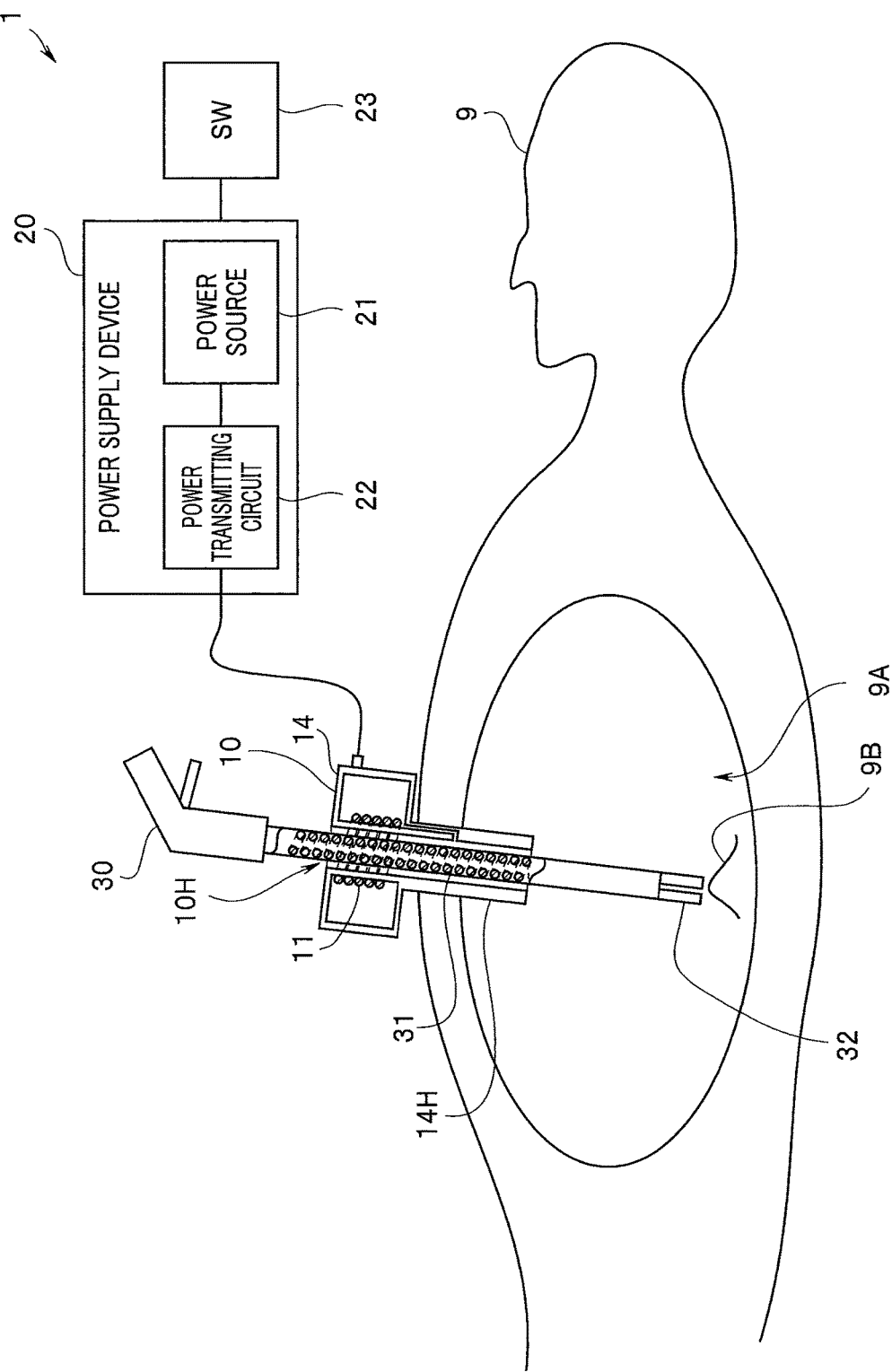
FIG. 1 is a schematic diagram for describing a usage condition of a medical system according to a first embodiment.

A treatment instrument 30 which is a medical instrument according to a first embodiment, a trocar 10 which is an insertion assisting tool and a medical system 1 will be described using FIG. 1 and FIG. 2. The trocar 10 and the treatment instrument 30 together with a power supply device 20 constitute a medical system 1. In the medical system 1, power is wirelessly transmitted/received via an alternating magnetic field. That is, the trocar 10 includes a power transmitter 16 configured to generate an alternating magnetic field and the treatment instrument 30 includes a power receiver 39 configured to wirelessly receive power via the alternating magnetic field and a treatment section 32 which is a drive circuit configured to be driven by the power received by the power receiver 39.

As will be described later, in the medical system 1 of the present embodiment, the treatment instrument 30 includes a power receiving coil 31 configured to generate minimal leakage electric field. The power receiving coil 31 of the power receiver 39 is magnetically coupled with the alternating magnetic field to receive power. The power receiving coil 31 is made up of a first counterclockwise power receiving coil 31L and a second clockwise power receiving coil 31R, and FIG. 2 two-dimensionally expresses this power receiving coil 31. That is, the first counterclockwise power receiving coil 31L is represented by a thin line and the second clockwise power receiving coil 31R is represented by a thick line, and the portion of the coil running on the front side of the drawing is represented by a solid line and the portion of the coil on the rear side of the drawing is represented by a dotted line. This representation method is likewise applicable to the following drawings.

First, the trocar 10 including the power transmitter 16 will be described. An elongated insertion tube 14H that extends from a base part of a case 14 of the trocar 10 is inserted into a subject 9. That is, the trocar 10 includes the insertion tube 14H which is a distal end portion punctured into the subject and a case 14 which is an extending portion disposed on a proximal end portion side of the distal end portion. An insertion hole 10H through which the treatment instrument 30 is inserted into the subject 9 is formed at a center of the case 14. The insertion hole 10H is a through hole that extends up to a distal end of the insertion tube 14H.

Upon receiving a supply of AC power from the power supply device 20 through operation of a switch 23 by the operator, the power transmitter 16 of the trocar 10 generates an alternating magnetic field.

The power supply device 20 that outputs the AC power to the power transmitter 16 of the trocar 10 includes a power source 21 and a power transmitting circuit 22. The power source 21 outputs large, high-frequency power of, for example, 10 W to 100 W. As shown in FIG. 2, the power transmitter 16 includes a solenoid-shaped power transmitting coil 11 wound around an outer circumferential portion of the insertion hole 10H and a power transmitting capacitor 15. The power transmitting coil 11 has a length of, for example, 10 mm to 50 mm.

The power transmitting coil 11 and the power transmitting capacitor 15 of the power transmitter 16 are connected in series and constitute an LC series resonance circuit on the power transmitting side configured to generate an alternating magnetic field of a predetermined resonance frequency FR1. The power source 21 outputs AC power of the resonance frequency FR1. Note that a configuration may be adopted in which a stray capacitance of the power transmitting coil 11 is used instead of the power transmitting capacitor 15. The power transmitting circuit 22 includes an impedance matching circuit (not shown) configured to perform impedance matching between the power source 21 and the resonance circuit.

Figure 2:
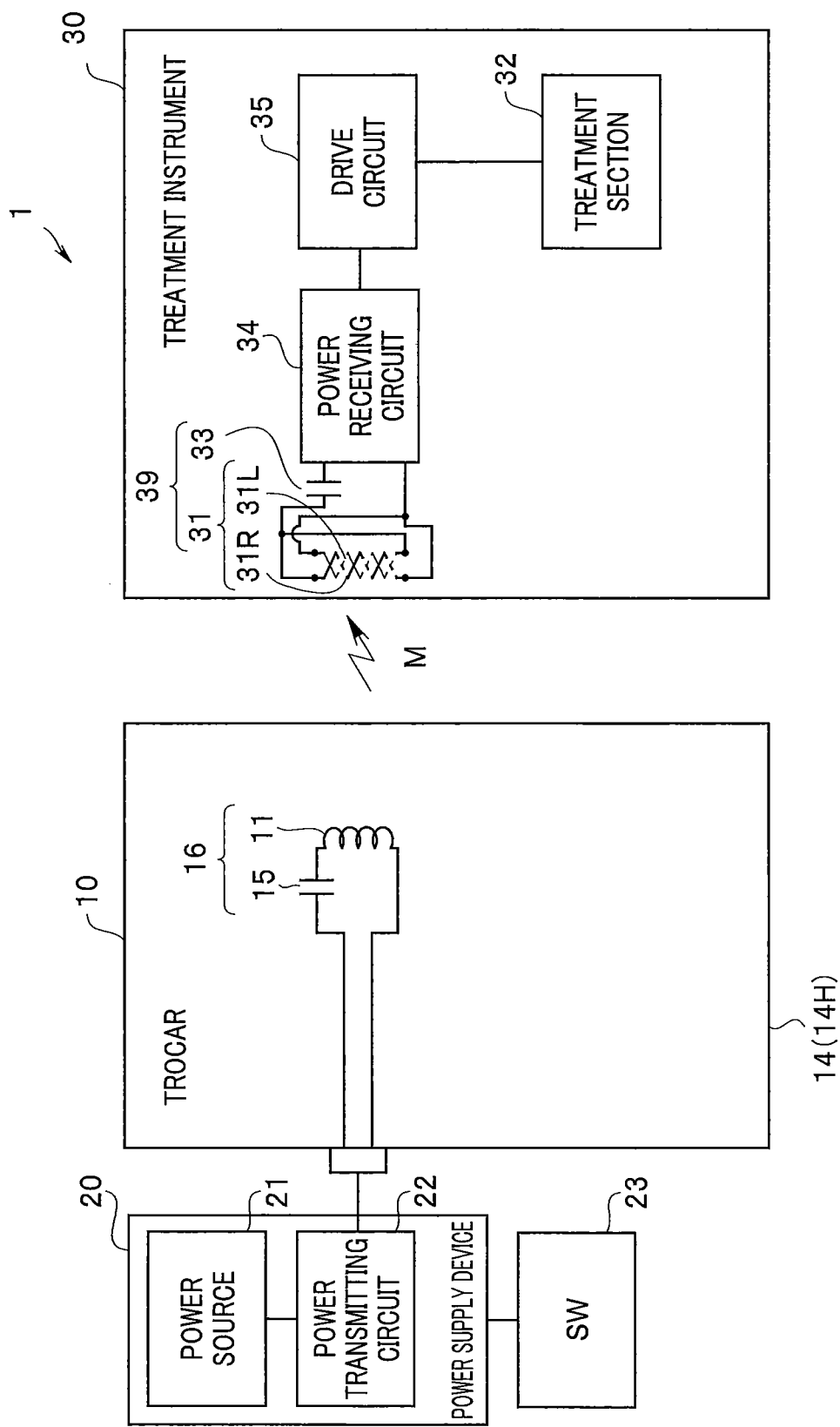
FIG. 2 is a configuration diagram of the medical system according to the first embodiment.

Note that according to FIG. 1 and FIG. 2, the power transmitting capacitor 15 is disposed in the trocar 10 and the power transmitting circuit 22 is disposed in the power supply device 20, but the power transmitting capacitor 15 and the power transmitting circuit 22 may also be disposed in the trocar 10 or may be disposed in the power supply device 20.

<Configuration of Treatment Instrument>

The insertion portion of the treatment instrument 30 is inserted into an abdominal cavity 9A which is the inside of the subject via the insertion hole 10H of the trocar 10. Note that in the medical system 1, an endoscope or the like is also inserted into the abdominal cavity 9A of the subject 9 via another trocar, but description thereof or the like will be omitted. The treatment instrument 30 is, for example, a high-frequency treatment instrument configured to apply high-frequency power to a treated part 9B such as a blood vessel tightly held to the treatment section 32 and thereby perform treatment such as dissection or coagulation. When inserted into the insertion hole 10H of the trocar 10, the treatment instrument 30 wirelessly receives power from the power transmitter 16 of the trocar 10. Since no cable for power source is connected thereto, the treatment instrument 30 has good operability.

As shown in FIG. 2, the treatment instrument 30 includes the power receiver 39, a power receiving circuit 34, a drive circuit 35 and a treatment section 32 which is the drive circuit. The power receiver 39 includes the power receiving coil 31 configured to inductively couple with the power transmitting coil 11 of the power transmitter 16 of the trocar 10 and wirelessly receive power via an alternating magnetic field.

The power receiving coil 31 is a solenoid-shaped coil disposed inside the insertion portion of the treatment instrument 30 along a longitudinal direction thereof, and the central axis thereof substantially coincides with a central axis of the insertion portion. The power receiving coil 31 has a length of, for example, 100 mm or more and 200 mm or less so that part thereof is always inserted in the power transmitting coil 11 during treatment or may be disposed throughout the overall length of the insertion portion. That is, the power receiving coil 31 is preferably longer than the power transmitting coil 11. This allows the treatment instrument 30 to always receive power by the power receiving coil 31 even when the treatment instrument 30 moves back and forth inside the insertion hole 10H during treatment. Note that the outer circumferential portion of the power receiving coil 31 is covered with, for example, insulating resin.

A power receiving capacitor 33 is connected in series to the power receiving coil 31, constituting an LC series resonance circuit on the power receiving side configured to efficiently receive an alternating magnetic field of a predetermined resonance frequency FR2. The resonance frequency FR2 of the power receiving side LC series resonance circuit is substantially the same as the resonance frequency FR1 of the transmitting side LC series resonance circuit and the medical system 1 efficiently performs wireless power transmission and reception through a magnetic field resonance phenomenon. Note that the resonance frequencies FR1 and FR2 can be selected from within a range of, for example, 100 kHz to 20 MHz as appropriate, but frequencies, use of which is legally authorized, such as 13.56 MHz are preferably selected.

Note that a configuration may also be adopted in which a stray capacitance of the power receiving coil 31 is used instead of the power receiving capacitor 33. The power receiving circuit 34 is configured to rectify and smooth an alternating current signal received by the power receiving coil 31, convert the rectified and smoothed alternating current signal to a DC signal, and further adjust the DC signal to a voltage to be supplied to the drive circuit 35 through a DC/DC converter. The power receiving circuit 34 includes an impedance matching circuit (not shown) for performing impedance matching between the drive circuit 35 and the resonance circuit. The drive circuit 35 converts the power from the power receiving circuit 34 to power suitable for driving the treatment section 32 and outputs the power. For example, the treatment section 32 of the high-frequency treatment instrument receives a supply of a drive signal having a frequency of 350 kHz and a voltage of several hundreds of Vpp used for treatment such as dissection or coagulation from the drive circuit 35.

Figure 3:
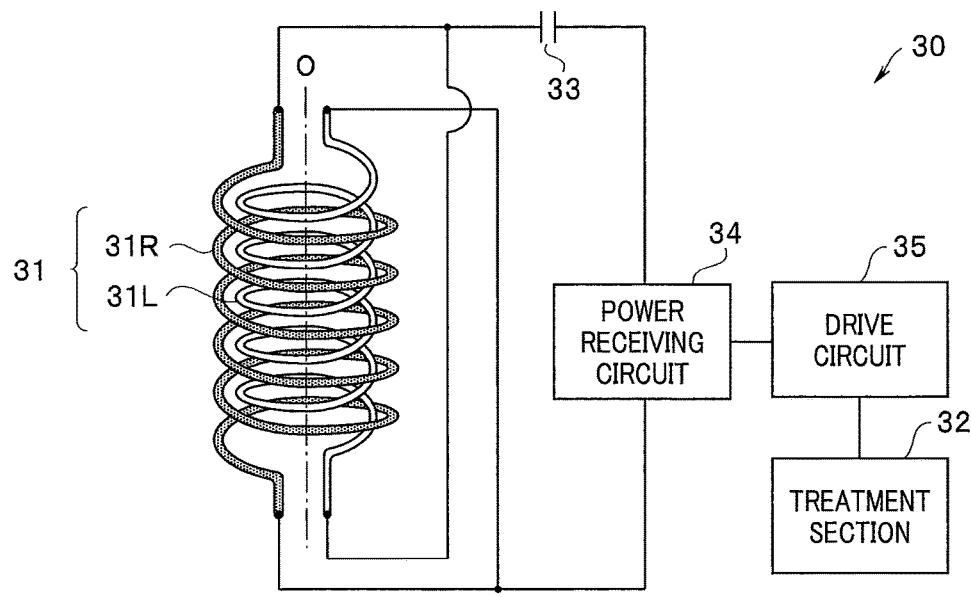
FIG. 3 is a configuration diagram of a treatment instrument according to the first embodiment.

As shown in FIG. 3, in the treatment instrument 30, the power receiving coil 31 is constructed of a first power receiving coil 31L and a second power receiving coil 31R. Note that FIG. 3 is a schematic diagram intended to provide description and the number of turns and the length or the like of the coil are different from those of the actual coil.

The second power receiving coil 31R and the first power receiving coil 31L of the power receiving coil 31 have solenoid shapes of the same length and the same number of turns, but have opposite winding directions. For example, while the first power receiving coil 31L is counterclockwise, the second power receiving coil 31R is clockwise.

The second power receiving coil 31R has a diameter slightly greater than a diameter of the first power receiving coil 31L and is arranged concentrically outside the first power receiving coil 31L. The two coils are electrically connected to the power receiving circuit 34 via the power receiving capacitor 33 so that directions of currents flowing through the respective coils are opposite to each other.

Here, the direction of the coil current means a direction in which the current comes out of the coil or a direction in which the current enters the coil at the terminal at a top end of the coil. In the present embodiment, the two coils are electrically connected in parallel as shown in FIG. 3.

The second power receiving coil 31R generates an alternating magnetic field of the same direction in the same space as a direction and space of an alternating magnetic field generated by the first power receiving coil 31L having a winding direction opposite to a winding direction of the second power receiving coil 31R.

When a magnetic flux that interlinks with the power receiving coil 31 is changed by an alternating magnetic field generated by the power transmitting coil 11 of the power transmitter 16 of the trocar 10, an induced electromotive force is generated in the power receiving coil 31, a coil current flows and power is received. In this case, the direction of the coil current flowing through the power receiving coil 31 is a direction in which the magnetic flux generated in the power receiving coil 31 by the coil current interferes with a change of the magnetic flux that interlinks with the power receiving coil 31.

For example, when a change of the interlinking magnetic flux of the power receiving coil 31 due to the alternating magnetic field generated by the power transmitting coil 11 at a certain time increases upward in an axial direction of the power receiving coil in FIG. 3, the coil current flows in a direction in which a downward magnetic flux is generated. Here, since the power receiving coil 31R and the power receiving coil 31L have opposite winding directions, the currents flowing through the two coils always flow in opposite directions (reverse phases). Therefore, the coil currents generate counter electromotive forces in opposite directions in the two coils, and potentials generated in the two coils are opposite to each other.

Figure 4:
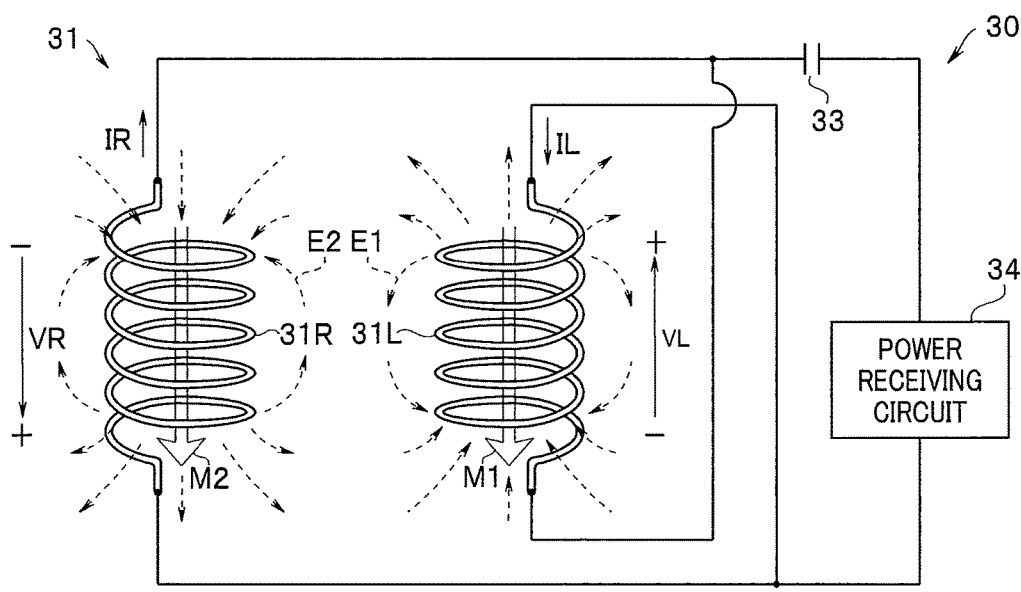
FIG. 4 is an exploded view of the power receiving coil of the treatment instrument according to the first embodiment.

For this reason, as shown in an exploded view in FIG. 4, upon receiving power, the first power receiving coil 31L and the second power receiving coil 31R generate alternating magnetic fields M1 and M2 of substantially the same intensity in the same direction in substantially the same space, and at the same time generate electric fields E1 and E2 of substantially the same intensity in opposite directions in substantially the same space.

That is, in the power receiving coil 31, the electric field E1 generated by the first power receiving coil 31L and the electric field E2 generated by the second power receiving coil 31R cancel each other out, thus drastically reducing an unnecessary leakage electric field generated around the power receiving coil. Therefore, it is also possible to drastically reduce the leakage electric field of the medical system 1 provided with the treatment instrument 30.

Note that the first power receiving coil 31L and the second power receiving coil 31R may preferably have substantially the same configuration so that the electric field E1 generated in the first power receiving coil 31L and the electric field E2 generated in the second power receiving coil 31R cancel each other out. For example, the length and the number of turns of the second power receiving coil 31R may differ from the length and the number of turns of the first power receiving coil 31L by ±10% respectively.

A common method used to reduce a leakage electric field is covering the perimeter of an apparatus with an electromagnetic shield made of an electric conductor such as a metal. However, covering with the electromagnetic shield, the entire treatment instrument 30 and the perimeter of the power receiving coil which is a source of the leakage electric field may eventually interrupt magnetic coupling between an alternating magnetic field generated in the power transmitting coil of the trocar and the power receiving coil of the treatment instrument and cause the efficiency of power transmission to considerably deteriorate, and therefore it is difficult to apply the electromagnetic shield.

However, the present configuration can reduce the leakage electric field without providing any electromagnetic shield that interrupts magnetic coupling between the power transmitting coil and the power receiving coil, and can thereby reduce an unnecessary leakage electric field for a medical instrument such as a treatment instrument and a rigid endoscope, for which it is difficult to provide an electromagnetic shield around the power receiving coil. That is, it is not necessary to provide an electric field shield and the insertion portion inserted into the subject 9 has a small diameter, and so the treatment instrument 30 is minimally invasive.

Note that as the treatment instrument 30, various types of bipolar treatment instruments may be used which include a treatment section that operates on power received by the power receiver 39. For example, an electric knife, high-frequency dissection forceps, high-frequency hemostasis forceps, hot biopsy forceps or a high-frequency coagulation treatment instrument may be used as the treatment instrument 30.

Furthermore, the treatment instrument 30 is not limited to a treatment instrument which carries out treatment by applying high-frequency power to the treated part 9B, but the treatment instrument 30 may be various types of electrically driven treatment instruments as well. For example, the treatment instrument 30 may be an ultrasound treatment instrument configured to dissect or coagulate a living tissue using ultrasound vibration, an ultrasound suction treatment instrument configured to crush and suction a living tissue using ultrasound vibration, an ablation treatment instrument configured to crush a living tissue using a rotary force of a drill or the like or a treatment instrument with an actuator having a function of electrically operating a distal end of forceps.

Furthermore, the medical instrument inserted into the insertion hole 10H of the trocar 10 is not limited to the so-called treatment instrument, but various types of medical instruments including an electrical drive circuit driven by electric power such as a rigid endoscope provided with an image pickup device such as a CCD and an illumination apparatus such as an LED as an electrical drive circuit may be suitably used as a medical instrument of the medical system of the present invention.

Modification of First Embodiment

Figure 5:
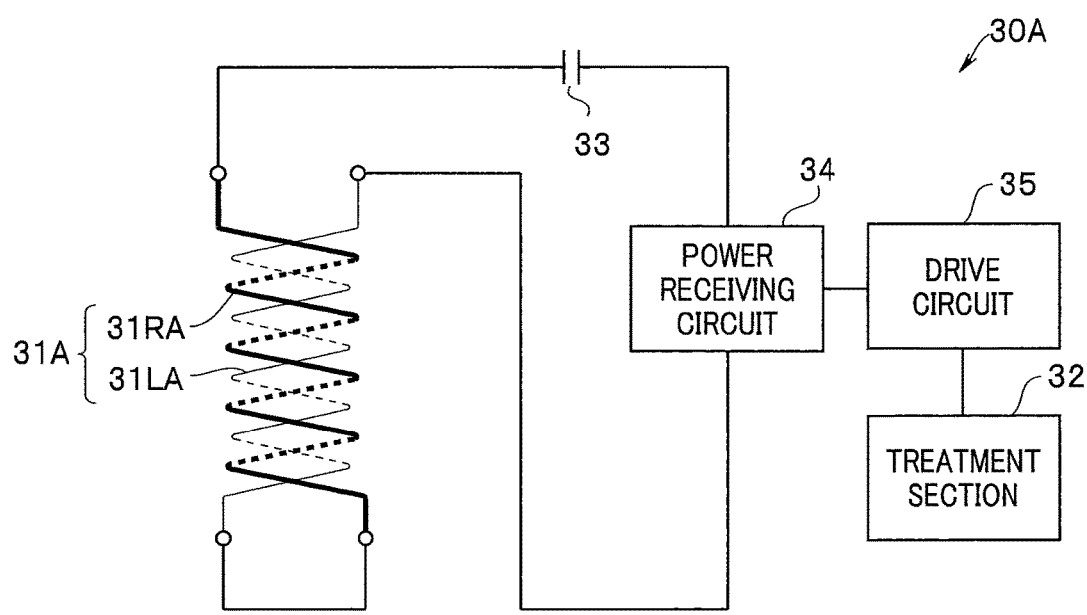
FIG. 5 is a configuration diagram of a treatment instrument according to a modification of the first embodiment.

In a power receiving coil 31A of a treatment instrument 30A according to a modification shown in FIG. 5, a first power receiving coil 31LA and a second power receiving coil 31RA are electrically connected in series. Here, the power receiving coil is disposed at the insertion portion of the treatment instrument, and the resonance capacitor and the power receiving circuit electrically connected to the power receiving coil are disposed on a proximal end side of the insertion portion of the treatment instrument.

The treatment instrument 30A in which the first power receiving coil 31LA and the second power receiving coil 31RA are connected in series has increased equivalent series resistance adding up the resistance of the two coils, compared to the treatment instrument 30 in which the first power receiving coil 31LA and the second power receiving coil 31RA are connected in parallel, but eliminates the need for wiring to connect the terminal on the distal end side of the insertion portion of the first power receiving coil 31L and the resonance capacitor on the proximal end side of the insertion portion, and wiring to connect the terminal on the distal end side of the insertion portion of the second power receiving coil 31R and the power receiving circuit on the proximal end side of the insertion portion, which would be necessary at the time of parallel connection. A reduction of the diameter can be easily achieved since fewer wires pass through the insertion portion of the treatment instrument.

Since the directions of coil currents during power reception are opposite to each other, the first power receiving coil 31LA and the second power receiving coil 31RA have electric field directions opposite to each other, and both electric fields cancel each other out, providing an effect of reducing an unnecessary leakage electric field around the power receiving coil as well as the treatment instrument 30.

Second Embodiment

Figure 6:
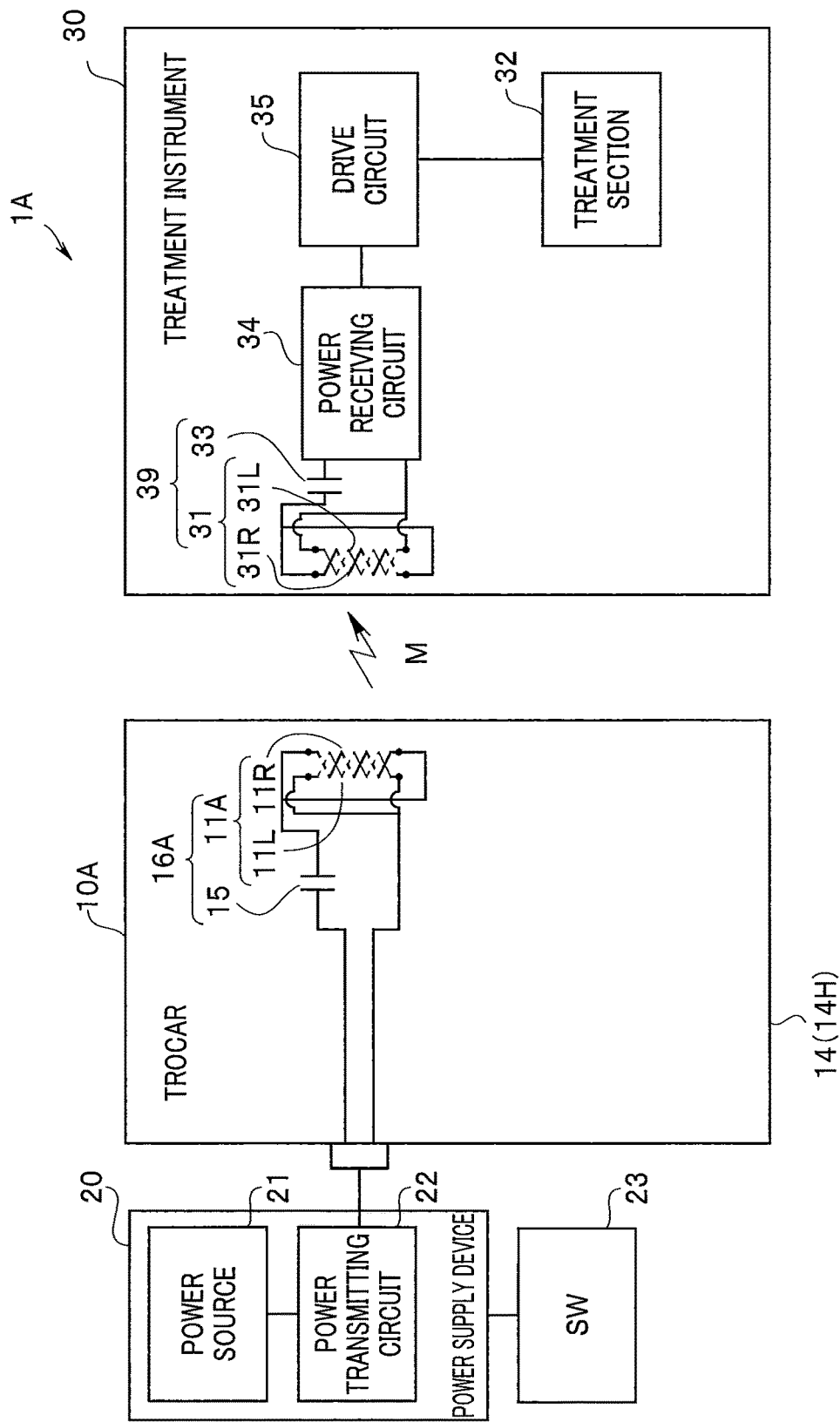
FIG. 6 is a configuration diagram of a medical system according to a second embodiment.

Next, a medical system 1A according to a second embodiment will be described using FIG. 6. The treatment instrument 30 of the medical system 1A has the same configuration as the configuration of the treatment instrument 30 of the medical system 1 and the medical system 1A is similar to the medical system 1 or the like, and therefore the same components are assigned the same reference numerals and description thereof will be omitted.

In the medical system 1A, a power transmitting coil 11A of a power transmitter 16A of a trocar 10A which is an insertion assisting tool is constructed of a first power transmitting coil 11L and a second power transmitting coil 11R having a winding direction opposite to a winding direction of the first power transmitting coil 11L, connected in parallel as in the case of the power receiving coil 31.

That is, the power transmitting coil 11A is constructed of the first solenoid-shaped power transmitting coil 11L and the second solenoid-shaped power transmitting coil 11R having substantially the same length and the same number of turns as those of the first power transmitting coil 11L but having an opposite winding direction. The first power transmitting coil 11L and the second power transmitting coil 11R having a diameter slightly greater than a diameter of the first power transmitting coil 11R are arranged concentrically at substantially the same position on the outer circumference of the insertion hole 10H of the trocar 10. Furthermore, the two coils are electrically connected in parallel and electrically connected to the power supply device 20 via the power transmitting resonance capacitor 15 so that currents flow through the respective coils in opposite directions.

When high-frequency power is supplied from the power supply device 20 to the power transmitter 16A, currents flow through the first power transmitting coil 11L and the second power transmitting coil 11R in opposite directions, but since their coils have opposite winding directions, magnetic fields generated in the respective coils are oriented toward the same direction.

On the other hand, since the coil currents flow in opposite directions, potentials generated in the respective coils are opposite to each other and electric fields generated around the respective coils have opposite directions.

Note that the first power transmitting coil 11L and the second power transmitting coil 11R may also be electrically connected in series.

In the trocar 10A, since the alternating magnetic field generated by the first power transmitting coil 11L and the alternating magnetic field generated by the first power transmitting coil 11R have the same direction, the two alternating magnetic fields are added up and applied to the treatment instrument 30. In contrast, since the electric field generated by the first power transmitting coil 11L and the electric field generated by the first power transmitting coil 11R have opposite directions, the two electric fields cancel each other out. That is, the alternating magnetic field generated in the power transmitting coils is not reduced when carrying out wireless power transmission from the power transmitter to the power receiver and only an unnecessary leakage electric field around the power transmitting coils is reduced. For this reason, the trocar 10A has less leakage electric field that leaks all over.

The medical system 1A provided with the trocar 10A and the treatment instrument 30, both of which have small leakage electric field can reduce leakage electric field more than the medical system 1.

The present invention is not limited to the aforementioned embodiments, but it goes without saying that the present invention may be modified, combined or applied in various ways without departing from the spirit and scope of the invention.

What is claimed is:
1. A medical instrument comprising:
a power receiver comprising a power receiving circuit configured to magnetically couple with an alternating magnetic field and receive power; and
a drive circuit configured to be driven by the power received by the power receiver,
wherein the power receiver comprises a first solenoid-shaped power receiving coil and a second solenoid-shaped power receiving coil having a winding direction opposite to a winding direction of the first power receiving coil, the first power receiving coil and the second power receiving coil have a same length and a same number of turns, and are arranged concentrically, the first power receiving coil and the second power receiving coil are electrically connected to the power receiving circuit so that a direction in which a current flows through the first power receiving coil is opposite to a direction in which a current flows through the second power receiving coil; and the first power receiving coil and the second power receiving coil are electrically connected in parallel.

2. The medical instrument according to claim 1, wherein the medical instrument is a treatment instrument or a rigid endoscope in which the first power receiving coil and the second power receiving coil are disposed at an insertion portion which is inserted into a body of a subject via an insertion hole of an insertion assisting tool.

3. An insertion assisting tool comprising a power transmitter configured to generate an alternating magnetic field to be applied to a medical instrument inserted into an insertion hole, wherein the power transmitter comprises a first solenoid-shaped power transmitting coil and a second solenoid-shaped power transmitting coil having a winding direction opposite to a winding direction of the first power transmitting coil, the first power transmitting coil and the second power transmitting coil have a same length and a same number of turns, and are arranged concentrically, the first power transmitting coil and the second power transmitting coil are electrically connected to a power supply device so that a direction in which a current flows through the first power transmitting coil is opposite to a direction in which a current flows through the second power transmitting coil; and wherein the first power transmitting coil and the second power transmitting coil are electrically connected in parallel.

4. The insertion assisting tool according to claim 3, wherein the insertion assisting tool is a trocar, a case of which has the insertion hole.

5. A medical system comprising:

an insertion assisting tool comprising a power transmitter configured to generate an alternating magnetic field; and a medical instrument comprising a power receiver comprising a power receiving circuit configured to magnetically couple with the alternating magnetic field when inserted into an insertion hole of the insertion assisting tool and receive power and a drive circuit configured to be driven by the power received by the power receiver, wherein the power receiver comprises a first solenoid-shaped power receiving coil and a second solenoid-shaped power receiving coil having a winding direction opposite to a winding direction of the first power receiving coil, the first power receiving coil and the second power receiving coil have a same length and a same number of turns and are arranged concentrically, the first power receiving coil and the second power receiving coil are electrically connected to the power receiving circuit so that a direction in which a current flows through the first power receiving coil is opposite to a direction in which a current flows through the second power receiving coil; and wherein the first power receiving coil and the second power receiving coil are electrically connected in parallel.

6. The medical system according to claim 5, wherein the first power receiving coil and the second power receiving coil are longer than a solenoid-shaped power transmitting coil of the power transmitter.

7. The medical system according to claim 6, wherein the power transmitter comprises a first solenoid-shaped power transmitting coil and a second solenoid-shaped power transmitting coil having a winding direction opposite to a winding direction of the first power transmitting coil, the first power transmitting coil and the second power transmitting coil have a same length and a same number of turns and are arranged concentrically, and the first power transmitting coil and the second power transmitting coil are electrically connected to a power supply device so that a direction in which a current flows through the first power transmitting coil is opposite to a direction in which a current flows through the second power transmitting coil.

8. The medical system according to claim 7, wherein the first power transmitting coil and the second power transmitting coil are electrically connected in parallel.

9. The medical system according to claim 5, wherein the medical instrument is a treatment instrument or a rigid endoscope, and the insertion assisting tool is a trocar, a case of which has the insertion hole.

* * * * *